United States Patent [19]

Verbrugge et al.

[11] 4,230,891
[45] Oct. 28, 1980

[54] 2-(2,2-DIHALOVINYL)-3,3-DIMETHYLCYCLOPROPANECARBALDEHYDE DIMETHYL ACETAL

[75] Inventors: Pieter A. Verbrugge; Petrus A. Kramer; Johannes Van Berkel; Hendrik C. Kelderman, all of Amsterdam, Netherlands

[73] Assignee: Shell Oil Company, Houston, Tex.

[21] Appl. No.: 966,681

[22] Filed: Dec. 5, 1978

[30] Foreign Application Priority Data

Dec. 16, 1977 [GB] United Kingdom ............... 52466/77

[51] Int. Cl.³ .......................................... C07C 43/313
[52] U.S. Cl. .................................... 568/591; 560/124; 568/303
[58] Field of Search .................... 560/124; 260/586 R; 568/591

[56] References Cited

U.S. PATENT DOCUMENTS 4,024,163  5/1977  Elliot .................................... 560/124

FOREIGN PATENT DOCUMENTS 1413491 11/1975 United Kingdom .

OTHER PUBLICATIONS

Salmond, Tetrahedron Letters, 14 pp. 1239–1240 (1977).

Combret, Tetrahedron Letters, 15 pp. 1035–1038 (1971).
Castro, Bull. Soc. Chem. Fr., No. 8, pp. 2770–2773 (1969).
Gilbert, Bull. Soc. Chem. Fr., No. 6 pp. 2047–2053 (1971).
Castro, Comptus. R., Acad. Sci. Ports, 268, Series C, pp. 1067–1069 (1969).
Ried, Ann., 679, pp. 51–55 (1964).

*Primary Examiner*—Natalie Trousof
*Assistant Examiner*—Michael Shippen

[57] ABSTRACT

New 2-(2,2-dihalovinyl)-3,3-dimethylcyclopropane derivatives of the formula

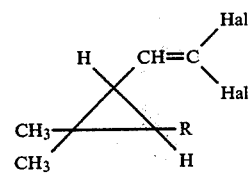

wherein each Hal is a halogen atom and R is dimethoxyethyl, 2-acetyl-3-oxobutyl, 2-methoxycarbonylpropyl or 2-acetyl-2-hydroxy-3-oxobutyl, are useful chemical intermediates for the preparation of pesticidally active cyclopropanecarboxylates.

3 Claims, No Drawings

2-(2,2-DIHALOVINYL)-3,3-DIMETHYLCYCLO-PROPANECARBALDEHYDE DIMETHYL ACETAL

BACKGROUND OF THE INVENTION

1. Field of the Invention

This invention relates to new 2-(2,2-dihalovinyl)-3,3-dimethylcyclopropane derivatives and to a process for the preparation of these derivatives.

2. Description of the Prior Art

Certain substituted cyclopropanecarboxylates are an important class of pesticides called "pyrethroids", which are of considerable interest because of their quick knock-down activity, low persistence as toxic residues and their low mammalian toxicity. However, the acid moiety of these pyrethroids has heretofore been fairly expensive to manufacture in the large scale quantities for agricultural and domestic applications.

The hereinafter described process of the invention and new intermediates provide a method for obtaining desired pyrethroids from 3-carene, which is an inexpensive, readily available, natural terpene found in numerous varieties of pine trees.

SUMMARY OF THE INVENTION

The present invention is directed to new 2-(2,2-dihalovinyl)-3,3-dimethylcyclopropane derivatives of the formula I

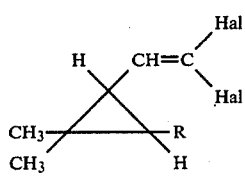

wherein each Hal is independently selected from chlorine, bromine or fluorine and R is a group selected from

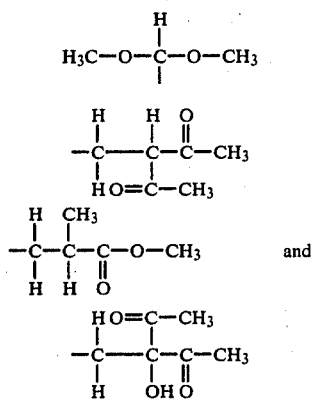

The groups named in (a), (b), (c) and (d) are called, respectively:
dimethoxymethyl,
2-acetyl-3-oxobutyl,
2-methoxycarbonylpropyl and
2-acetyl-2-hydroxy-3-oxobutyl.

Examples of compounds of formula I are:
3-(2,2-dichlorovinyl)-2,2-dimethylcyclopropanecarbaldehyde dimethyl acetal,
1-(2-acetyl-3-oxobutyl)-2-(2,2-dichlorovinyl)-3,3-dimethylcyclopropane,
1-(2,2-dichlorovinyl)-2-(2-methoxycarbonylpropyl)-3,3-dimethylcyclopropane
1-(2-acetyl-2-hydroxy-3-oxobutyl)-2-(2,2-dichlorovinyl)-3,3-dimethylcyclopropane
3-(2,2-dibromovinyl)-2,2-dimethylcyclopropanecarbaldehyde dimethyl acetal
3-(2,2-difluorovinyl)-2,2-dimethylcyclopropanecarbaldehyde dimethyl acetal and
3-(2-chloro-2-fluorovinyl)-2,2-dimethylcyclopropanecarbaldehyde dimethyl acetal The invention also relates to a process for the preparation of compounds of formula I, which process comprises two steps, the first step in treating a tri(dialkylamino)phosphine or an alkyl ester of an ortho-phosphorous acid bis(dialkylamide) with a compound generating a dihalocarbene - which reaction is allowed to proceed to virtual completion - and the second step consisting of treating the product resulting from the first step with an aldehyde of formula II

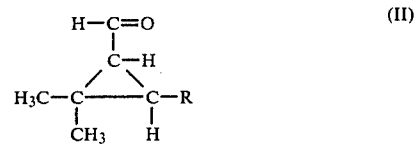

wherein R has the same meaning as in formula I.

The highest yields of the compounds of formula I have been obtained when R is formula II represented a dimethoxymethyl group.

The alkyl groups present in the tri(dialkylamino)-phosphine or the alkyl ester of an ortho-phosphorous acid bis(dialkylamide) may be the same or different and linear or branched and contain from 1 to 10 carbon atoms. The alkyl groups are suitably the same, and preferably have less than six carbon atoms and more preferably less than three carbon atoms. The use of tri(dialkylamino)phosphines is preferred, because they usually afford the compounds of formula I in a higher yield than the alkyl esters of ortho-phosphorous acid bis(dialkylamides) (the latter compounds are obtained by replacing one of the dialkylamino groups in a tri(-dialkylamino)phsophine by an alkoxy group). Tri(diethylamino)phosphine and tri(dimethylamino)phosphine are most preferred.

Tri(dialkylamino)phosphines may easily be prepared by reaction of a dialkylamine with a phosphorous trihalide, as described in "Organic Synthesis", Coll. Vol V (1973) 602–603. This reaction results in the formation of a solution of the tri(dialkylamino)phosphine which also contains precipitated dialkylammonium halide. Filtration of the precipitate and distillation of the filtrate yields a fraction of pure tri(dialkylamino)phosphine.

Applicants have tried to avoid the preparation of pure tri(dialkylamino)phosphine by contacting the solution containing the precipitate with the aldehyde of formula II, but this procedure afforded only a very small amount of the compound of formula I, if any. It has now been found that this solution, itself, contains compounds which prevent the reaction with the aldehyde of formula II and that these compounds can easily be removed. Accordingly, a preferred embodiment of the present invention comprises reacting a dialkylamine with a phosphorous trihalide in the presence of a solvent that is substantially inert, washing the resulting reaction mixture with water or dilute aqueous mineral acid (e.g. hydrochloric acid, sulphuric acid or the like (whether or not after prior separation of the precipitated dialkylammonium halide) and reacting the tri(dialkylamino)phosphine dissolved in the washed solution with the compound generating a dihalocarbene. This embodiment usually affords the compounds of formula I in the highest yield. It is not necessary to separate the precipitated dialkylammonium halide prior to washing, because this salt is water-soluble. The yield of the compound of formula I can be further enhanced by drying the washed liquid, for example over a solid drying agent such as anhydrous sodium sulphate or anhydrous magnesium sulphate.

Another attractive feature of the process according to the present invention is that it may be carried out in the presence of alkane solvents, for example, in alkane solvents with a boiling point or boiling range up to 200° C. This also applies to the said reaction between a dialkylamine and a phosphorous trihalide. Examples of alkane solvents are those containing from 5 to 10 carbon atoms, for example, pentane, hexane, heptane, octane and nonane. Mixtures of alkanes are very suitable, for example gasolines having a boiling range from 62° C. to 82° C. or from 80° C. to 110° C. If desired, the process may be carried out in substantially inert solvents other than alkanes, for example in tetrahydrofuran.

Examples of compounds generating a dihalocarbene under the conditions of the process according to the present invention are carbon tetrahalides, chloroform, bromoform and iodoform. Very good results have been obtained with carbon tetrahalides. Examples of carbon tetrahalides are carbon tetrachloride, carbon tetrabromide, carbon tetraiodide, bromotrichloromethane (forming dichlorocarbene) and dibromodifluoromethane (forming difluorocarbene). Very good results have been obtained with carbon tetrachloride.

Both steps of the process according to the present invention are preferably carried out at a temperature in the range of from −50° C. to +50° C., particularly at temperatures of from −20° C. to +35° C.

The aldehydes of formula II may have a cis or trans structure or may be a mixture of such isomers, a pure optical isomer or a mixture of optical isomers.

The process may be carried out in the liquid phase by adding a tri(dialkylamino)phosphine or an alkyl ester of an ortho-phosphorous acid bis(dialkylamide) to a compound generating a dihalocarbene, if desired dissolved in a solvent that is substantially inert, for example in an alkane solvent, and stirring the mixture thus obtained until the first step has been substantially completed, which may take from 1 to 60 minutes. Then, the aldehyde of formula II is added to the mixture and stirring continued for 1 to 60 minutes until the second step has been completed. Dihalophosphoranes and phosphine oxides can be removed from the reaction mixture by washing. This washing can be carried out with water when tri(dimethylamino)phosphine has been used, but when a tri(dialkylamino)phosphine having two or more carbon atoms in the alkyl groups has been used, dilute aqueous hydrochloric acid is more suitable than water. Therefore, tri(dimethylamino)phosphine is the most preferred tri(dialkylamino)phosphine. The washed reaction mixture is dried and the solvent is evaporated from the dried solution to leave a residue, which may be further purified, for example by distillation, to obtain the compound of formula I in a pure state.

As mentioned earlier, the compound of formula I, wherein R is dimethoxymethyl, is prepared by a multi-step synthesis from the natural terpene, 3-carene. This multi-step synthesis is as follows:

Step 1

Ozonolysis of 3-carene, followed by reduction of the ozonolysis product formed (for example with dimethyl sulphide) in the presence of methanol and an acetalizing catalyst (for example p-toluenesulphonic acid) yields 1-(2,2-dimethoxyethyl)-2,2-dimethyl-3-(2-oxopropyl)-cyclopropane. Ozonolysis of organic compounds and reduction of the peroxidic ozonolysis products formed is described in, for example, Chemical Reviews 58 (1958) 925–995. When the starting material is (+)-3-carene the products have a cis isomer form.

Step 2

Oxidation of compound from step 1 above with a per-acid in the presence of a solvent yields (2-(2,2-dimethoxyethyl)-3,3-dimethylcyclopropyl)methyl acetate. Oxidations of ketones to esters are described in "Methoden der Organischen Chemie", Volume VIII (1952) 559–560. Examples of suitable per-acids are perbenzoic acid, 3-chloroperbenzoic acid and peracetic acid.

Step 3

Hydrolysis of the compound from step 2 above in the presence of, for example, acetic acid, yields (2,2-dimethyl-3-(2-formylethyl)cyclopropyl)methyl acetate. Hydrolysis of acetals to aldehydes is described in "Methoden der Organischen Chemie" (Houben-Weyl), Volume VII, part 1 (1954) 423–428.

Step 4

Reaction of the compound from step 3 above with acetic anhydride in the presence of an amine, for example triethylamine or of an acetate of a strong base, for example sodium acetate, yields the enol acetate 2-(3-acetoxymethyl-2,2-dimethylcyclopropyl)vinyl acetate. Preparation of enol acetates from anhydrides is described in "Methoden der Organishchen Chemie" (Houben-Weyl), Volume VIII (1952) 552.

Step 5

Ozonolysis of the compound from step 4 above, followed by reduction of the ozonolysis product formed (for example with dimethyl sulphide) in the presence of methanol and an acetalizing catalyst (for example p-toluenesulphonic acid) yields 3-acetoxymethyl-2,2-dimethylcyclopropanecarbaldehyde dimethyl acetal. This compound is claimed in British patent application No. 52465/77, filed Dec. 16, 1977, in Great Britain and in a corresponding U.S. application Ser. No. 965,951 to Johannes Van Berkel and Hendrik C. Kelderman.

Step 6

Hydrolysis of the compound from step 5 above yields 3-hydroxymethyl-2,2-dimethylcyclopropanecarbaldehyde dimethyl acetal. This compound is claimed in British patent application No. 52464/77, filed Dec. 16, 1977, in Great Britain and in a corresponding U.S. application Ser. No. 965,951 to Johannes Van Berkel and Hendrik C. Kelderman. Hydrolysis of esters is described in, fo example, "Methoden der Organischen Chemie" (Houben-Weyl), Volume VIII (1952), 418–423 and 638–639.

Step 7

Oxidation of the compound from step 6 above yields 3-formyl-2,2-dimethylcyclopropanecarbaldehyde dimethyl acetal. This compound is claimed in British patent application No. 52463/77 filed Dec. 16, 1977 in Great Britain and in a corresponding U.S. application Ser. No. 965,951 to Johannes Van Berkel and Hendrik C. Kelderman. The oxidation of primary alcohols to aldehydes is described in, for example, "Methoden der Organischen Chemie", Vol. VII, Part 1 (1954) 159–192. The oxidation is suitably carried out with the chromium trioxide-pyridine complex, as described in J. Org. Chem. 35 (1970) No. 11, 4000–4002.

As mentioned earlier the dihalovinylcyclopropyl derivatives prepared by the process of the invention are useful intermediates for pyrethroid synthesis. Thus, hydrolysis of, e.g., 3-(2,2-dihalovinyl)-2,2-dimethylcyclopropanecarbaldehyde dimethyl acetals, in the presence of, for example, acetic acid, followed by oxidation with, for example, hydrogen peroxide in alkaline medium, of the aldehyde formed yields a 3-(2,2-dihalovinyl)-2,2-dimethylcyclopropanecarboxylic acid, esters of which are synthetic pyrethroids disclosed in U.S. Pat. No. 4,024,163.

The starting aldehydes of formula II in which R represents a 2-acetyl-3-oxobutyl, a 2-methoxycarbonylpropyl or a 2-acetyl-2-hydroxy-3-oxobutyl group may be prepared as described in U.S. Pat. No. 3,708,528, by ozonolysis of 4-acetyl-2-carene followed by reduction of the ozonolysis product formed. Applicants have found that this procedure not only yields 1-(2-acetyl-3-oxobutyl)-2-formyl-3,3-dimethylcyclopropane but also 1-formyl-2-(2-methoxycarbonylpropyl)-3,3-dimethylcyclopropane and 1-(2-acetyl-2-hydroxy-3-oxobutyl)-2-formyl-3,3-dimethylcyclopropane.

ILLUSTRATIVE EMBODIMENTS

The following Embodiments further illustrate the compounds of the invention and their preparation. Yields and purities were determined by means of gas-liquid chromatography and nuclear magnetic resonance (NMR) spectroscopy. The NMR data quoted were recorded at 90 MHz using solutions of the compounds in deuterochloroform.

EMBODIMENT 1

1-(2,2-Dimethoxyethyl)-2,2-dimethyl-3-(2-oxopropyl)-cyclo propane

A flask was charged with (+)-3-carene (375 mmol) and water-free methanol (150 ml) and kept at a temperature of −60° C. Then, a mixture of ozone and oxygen was passed through the liquid in the flask at a rate of 70 l/h (corresponding to 75 mmol of ozone per hour) until the (+)-3-carene was fully converted (5 hours). The reaction mixture formed was allowed to adopt a temperature of 20° C., dimethyl sulphide (750 mmol) and p-toluenesulphonic acid (1.74 mmol) were added and the mixture formed was stirred for four days at 20° C. At the end of this period, the (+)-3-carene was fully converted into the desired product. Methanol and dimethyl sulphide were evaporated from the reaction mixture, at a pressure of 24 mbar (40° C.), diethyl ether (150 ml) was added to the residue obtained, the solution formed was washed with a 5%w aqueous solution of sodium hydrogen carbonate (30 ml) and with four 30 ml portions of water, the washed solution was dried over anhydrous magnesium sulphate, and the solvent was evaporated from the dried liquid at a temperture of 30° C. and a pressure of 24 mbar to give a residue (68.9 g). This residue was distilled at 83° C./1 mbar to give a fraction consisting of the cis isomer of the desired product, yield 73.5%.

EMBODIMENT 2

(2-(2,2-Dimethoxyethyl)-3,3-dimethylcyclopropyl)-methyl acetate

The contents of a flask charged with the product as prepared in Embodiment 1 above (200 mmol), chloroform (300 ml) and 3-chloroperbenzoic acid (384 mmol) were stirred at 20° C. for 24 hours. The precipitate formed was separated by filtration, the filtered precipitate was mixed with n-pentane (150 ml), the mixture was separated by filtration, the combined filtrates were washed with two 50 ml portions of a 5% solution of sodium carbonate in water and with two 50 ml portions of water, the washed liquid was dried over anhydrous magnesium sulphate, and the solvent was evaporated from the dried liquid at a temperature of 90° C. and a pressure of 20 mbar to give a residue containing the desired product in a yield of 97%. The content of the desired product in the residue was 92%; only the cis isomer had been formed.

EMBODIMENT 3

(2,2-Dimethyl-3-(2-formylethyl)cyclopropyl)methyl acetate

The contents of a flask charged with the product in the residue prepared in Embodiment 2 above (218 mmol in the residue prepared as described in 2), acetic acid (40 ml) and water (20 ml) were stirred at 60° C. during 2.5 hours. The solvent was evaporated from the reaction mixture at a temperature of 45° C. and a pressure of 24 mbar, the residue obtained was taken up in diethyl ether (150 ml), the solution obtained was washed with two 50 ml portions of a 5%w solution of sodium hydrogen carbonate in water and with two 50 ml portions of water, the washed solution was dried over anhydrous magnesium sulphate, and the solvent was evaporated from the dried liquid at a temperature of 30° C. and a pressure of 24 mbar to give a residue containing the desired product in a yield of 80%; the content of the desired product in the residue was 85%. Only the cis isomer had been formed.

EMBODIMENT 4

2-(3-Acetoxymethyl-2,2-dimethylcyclopropyl)vinyl acetate

The contents of a flask charged with the product in the residue prepared in Embodiment 3 above (175 mmol, triethylamine (386 mmol) and acetic anhydride (350 ml) were stirred at 20° C. for 18 hours. The solvent was evaporated from the reaction mixture at a temperature of 50° C. and a pressure of 20 mbar, the residue obtained was taken up in diethyl ether (150 ml), the solution obtained was washed with five 40 ml portions of water, the washed solution was dried over anhydrous magnesium sulphate and the solvent was evaporated from the dried liquid at a temperature of 40° C. and a pressure of 20 mbar to give a residue containing the desired product in quantitative yield. The content of the desired product in the residue was 88.4%; 64% of the desired product had the cis structure, 36% the trans structure on the carbon-carbon double bond. The orientation to the cyclopropane ring was still cis.

EMBODIMENT 5

3-Acetoxymethyl-2,2-dimethylcyclopropanecarbaldehyde dimethyl acetal

A flask was charged with the product in the residue prepared in Embodiment 4 above (175 mmol), water-free methanol (200 ml) and p-toluenesulphonic acid (1.16 mmol) and kept at a temperature of −65° C. Then, a mixture of ozone and oxygen was passed through the liquid in the flask at a rate of 60 l/h (corresponding to 70 mmol of ozone per hour) until the starting material (product of Embodiment 4 above) was fully converted (2.5 hours). The reaction mixture formed was allowed to adopt a temperature of 20° C., dimethyl sulphide (350 mmol) was added and the mixture formed was stirred for 17 hours at 20° C. Methanol and dimethyl sulphide were evaporated from the reaction mixture, at a pressure of 16 mbar, diethyl ether (50 ml) was added to the residue obtained, and sufficient saturated aqueous solution of sodium bicarbonate was added to the mixture so that the pH reached a value of 7. Then, the mixture was washed with three 50-ml portions of water, the washed liquid was dried over anhydrous magnesium sulphate, and the solvent was evaporated from the dried liquid at a temperature of 40° C. and a pressure of 24 mbar to give a residue (29.6 g) containing the desired product (yield between 51 and 78%). Only the cis isomer had formed. The NMR spectrum of the desired product showed the following absorptions:

| | |
|---|---|
| $\partial$ = 3.38 ppm (singlet, C—O—CH$_3$) | $\partial$ = 1.18 ppm (singlet, H$_3$C—C—CH$_3$) |
| $\partial$ = 4.2 ppm (multiplet, H—C—O—CH$_3$) | $\partial$ = 1.1 ppm (multiplet, H—C—CH$_2$) |
| $\partial$ = 1.2 ppm (multiplet, H—C—C(H)—(OCH$_3$)$_2$) | $\partial$ = 4.2 ppm (multiplet, H—C—CH$_2$) |
| $\partial$ = 1.18 ppm (singlet H$_3$C—C—CH$_3$) | $\partial$ = 2.1 ppm (singlet, H$_3$C—C(O)—O—) |

EMBODIMENT 6

3-Hydroxymethyl-2,2-dimethylcyclopropanecarbaldehyde dimethyl acetal

A flask was charged with all of the residue obtained in Embodiment 5, water (75 ml), sodium hydroxide (150 mmol) and acetone (25 ml) and the liquid obtained was kept under reflux (60° C.) for three hours. Then, the acetone and part of the water were evaporated at a pressure of 16 mbar, the residue obtained was extracted with five 50-ml portions of diethyl ether (during the last two extractions sufficient sodium chloride was added so that the aqueous phase was saturated with this salt), the combined five extract phases were dried over anhydrous magnesium sulphate, and the solvent was evaporated from the dried liquid at a temperature of 40° C. and a pressure of 24 mbar to give a residue containing the desired product in a yield of 51%, calculated on product of Embodiment 4. The content of the desired product in the residue was 80%. The cis content of the desired product was 70%.

The NMR spectrum of the cis isomer of the desired product showed the following absorptions:

| | |
|---|---|
| $\partial$ = 3.32 ppm (singlet, C—O—CH$_3$) | $\partial$ = 1.05 ppm (singlet, H$_3$C—C—CH$_3$) |
| $\partial$ = 4.83 ppm (doublet, H—C—O—CH$_3$) | $\partial$ = 1.2 ppm (multiplet, H—C—CH$_2$) |
| $\partial$ = 1.53 ppm (doublet, H—C—C(H)—(OCH$_3$)$_2$) | $\partial$ = 3.8 ppm (doublet, H$_2$C—OH) |
| $\partial$ = 1.05 ppm (singlet, H$_3$C—C—CH$_3$) | $\partial$ = 4.3 ppm (singlet, H$_2$C—OH) |

EMBODIMENT 7

3-Formyl-2,2-dimethylcyclopropanecarbaldehyde dimethyl acetal

A flask was charged with a mixture of pyridine (120 mmol) and methylene chloride (150 ml) and then with chromium trioxide (60 mmol), at a temperature of 20° C. The contents of the flask were stirred for 15 minutes. Then, a solution of 1.74 g of the residue of Embodiment 6—which contained 6.39 mmol of the product prepared in Embodiment 6 above—in methylene chloride (5 ml) was added to the contents of the flask and stirring was continued for 20 minutes. The precipitate in the flask was allowed to settle, the liquid in the flask was decanted, the precipitate was washed with three 25-ml portions of diethyl ether, the three washings were filtered over a bed of 2 cm Florisil (trademark), the combined three filtrates were washed with two 20-ml portions of a 5%w aqueous solution of sodium hydroxide and then with two 20-ml portions of water, and the combined washed ethereal liquids were added to the decanted liquid. The liquid thus obtained was dried over anhydrous magnesium sulphate and the solvent was evaporated from the dried liquid at a pressure of 16 mbar to give a residue containing the desired product in a yield of 59%, calculated on starting material (product of Embodiment 6). The content of the desired product in the residue was 46.5%. The cis content of the desired product was 70%.

The NMR spectrum of the cis isomer of the desired product showed the following absorptions:

| | |
|---|---|
| = 3.30 ppm (singlet, C—O—CH$_3$) | = 1.8 ppm (doublet, H—C—C(O)H) |
| = 4.8 ppm (doublet, H—C—O—CH$_3$) | = 9.6 ppm (doublet, H—C=O) |
| = 1.2 ppm (multriplet, H—C—C(H)—(OCH$_3$)$_2$) | |
| = 1.22 ppm (singlet, H$_3$C—C—CH$_3$) | |
| = 1.37 ppm (singlet, H$_3$C—C—CH$_3$) | |

EMBODIMENT 8

Preparation of 3-(2,2-dichlorovinyl)-2,2-dimethylcyclopropanecarbaldehyde dimethyl acetal Tri(dimethylamino)phosphine (48 mmol) was added to a solution of carbon tetrachloride (48 mmol) in pentane (100 ml) at a temperature of 3° C. The mixture obtained was stirred for 10 minutes at a temperature between 3° C. and 5° C. This ended the first step. Then, the product of Embodiment 7 (24 mmol, present in the residue prepared as described in Embodiment 7) was added over a period of 10 minutes, the temperature was allowed to rise to 13° C. and stirring was continued for 15 minutes. This ended the second step. The reaction mixture was washed with water (20 ml), the mixture formed was allowed to separate into an aqueous and an organic phase, and the organic phase was isolated and dried over anhydrous sodium sulphate. The solvent was evaporated from the dried organic liquid, giving a residue containing the desired product in a yield of 77%. The content of the desired product in the residue was 47%. The cis content of the desired product was 70%. The NMR spectrum of the desired product showed the following absorptions:

| | |
|---|---|
| = 3.34 ppm (singlet, C—O—CH₃) | = 1.7 ppm (double doublet, H—C—C(H)=C) |
| = 4.3 ppm (doublet, H—C—O—CH₃) | = 5.83 ppm (doublet, cis H—C=C) |
| = 1.2 ppm (multiplet, H—C—(H)— (OCH₃)₂) cis = 1.14 ppm (singlet, H₃C—C—CH₃); trans = 1.22 ppm cis = 1.29 ppm (singlet, H₃C—C—CH₃); trans = 1.22 ppm | = 5.72 ppm (doublet, trans H—C=C) |

EMBODIMENT 9

Preparation of 3-(2,2-dichlorovinyl)-2,2-dimethylcyclopropanecarbaldehyde dimethyl acetal using pre-prepared tri(dimethylamino)phosphine (a) Preparation of tri(dimethylamino)phosphine A solution of dimethylamine (2.22 mol) in pentane (350 ml) was added with stirring over a period of 20 minutes to a solution of phosphorous trichloride (0.327 mol) in pentane (200 ml) at a temperature 37° of −20° C. This caused the formation of a white precipitate of dimethylamine hydrochloride and a temperature rise to +18° C. The mixture was stirred for 20 hours at 20° C., cooled to 0° C., and the suspension was extracted with water (150 ml). The raffinate phase obtained was dried over anhydrous sodium sulphate, the sodium sulphate was filtered off and washed with pentane to give a solution (in total 580 ml) containing tri(dimethylamino)phosphine (yield 70%).

(b) Preparation of 3-(2,2-dichlorovinyl)-2,2-dimethylcyclopropane carbaldehyde dimethyl acetal The experiment described in Embodiment 8 was repeated but started with the addition of a solution of tri(dimethylamino)phosphine (48 mmol) in pentane (122 ml), which solution was prepared as described in section (a) of Embodiment 9, to carbon tetrachloride (48 mmol). The yield of the desired product in the residue was again 77%.

EMBODIMENT 10

(a) 1-(2-Acetyl-3-oxobutyl)-2-formyl-3,3-dimethylcyclopropane (b) 1-Formyl-2-(2-methoxycarbonylpropyl)-3,3-dimethylcyclopropane (c) 1-(2-Acetyl-2-hydroxy-3-oxobutyl)-2-formyl-3,3-dimethylcyclopropane A 100-ml three-necked flask provided with a magnetic stirrer, thermometer, inlet for ozone, and a calcium chloride tube was charged with 4-acetyl-2-carene (60 mmol), water-free methanol (1.55 g) and water-free dichloromethane (75 ml) and then with potassium carbonate powder (0.25 g), and the reaction mixture was kept at a temperature of −70° C. Then, a mixture of ozone and oxygen was passed through the liquid in the flask at a rate of 40 l/h until all of the 4-acetyl-2-carene has been converted (65 min.). Then, dimethyl sulphide (122 mmol) was added, the flask was allowed to adopt a temperature of 20° C., and stirring was continued until all the peroxide had reacted (2.5 hours). The reaction mixture was washed until neutral with a saturated aqueous solution of sodium bicarbonate, the organic phase was isolated, the isolated organic phase dried over anhydrous magnesium sulphate, and the solvent was evaporated from the dried organic liquid, leaving 12.7 g of a residue.

A solution of sulphuric acid (34 mmol) in water (10 ml) was added with stirring to a solution of sodium sulphite (68 mmol) in water (40 ml). An amount of 7.1 g of the residue was added to the mixture thus obtained and stirring was continued for 30 minutes at 20° C. The reaction mixture obtained was washed with three 25-ml portions of dichloromethane. A solution of sodium carbonate (40 mmol) in water (20 ml) was added to the washed aqueous solution, which caused the formation of an oily layer. Extraction of the mixture thus obtained with three 25-ml portions of dichloromethane, drying of the combined extract phases over anhydrous magnesium sulphate, and evaporation of the solvent from the dried liquid gave 2.9 g of a residue containing the aldehydes (a), (b) and (c) in a total yield of 22%, calculated on starting 4-acetyl-2-carene. The three aldehydes had the cis structure.

EMBODIMENT 11

(a) 1-2-Acetyl-3-oxobutyl-2-(2,2-dichlorovinyl)-3,3-dimethylcyclopropane (b) 1-(2,2-Dichlorovinyl)-2-(2-methoxycarbonylpropyl)-3,3-dimethylcyclopropane (c) 1-(2-Acetyl-2-hydroxy-3-oxobutyl-2-(2,2-dichlorovinyl)-3,3-dimethylcyclopropane Tri(dimethylamino)phosphine (30 mmol) was added in two minutes to a solution of carbon tetrachloride (30 mmol) in pentane (25 ml) at 20° C., while the flask was cooled with tap water. This addition resulted in a temperature rise to 35° C. and in the formation of a white precipitate. The mixture was allowed to adopt a temperature of 20° C. This ended the first step. Subsequently, the aldehyde mixture (2.8 g) prepared in Embodiment 10 was added in two minutes time and stirring was continued for 2.5 hours at 20°C. This ended the second step. The reaction mixture was washed with water (50 ml), the organic phase was isolated, washed with three 25-ml portions of water and dried over anhydrous magnesium sulphate. The solvent was evaporated from the dried organic liquid, giving a residue (2.15 g) having the following composition:

| Compound a | 17%m |
| Compound b | 31%m |
| Compound c | 40%m |
| starting aldehydes | 12%m |

The residue was mixed with a solution of sodium sulphite (13 mmol) in water (10 ml) and a solution of sulphuric acid (8 mmol) in water (2.5 ml) and the mixture obtained was stirred for 65 hours. The reaction mixture obtained was extracted with two 25-ml portions of dichloromethane and the combined extract phases were dried over anhydrous magnesium sulphate. The solvent was evaporated from the dried organic liquid, leaving a residue (1.6 g) with the following composition:

| Compound a | 23%m | Compound c | 34%m |
| Compound b | 37%m | balance | 6%m |

The residue was subjected to microdistillation to give the following fractions:

| Boiling Range, 0° | Pressure, mbar | Content of Compounds, % m | | |
| --- | --- | --- | --- | --- |
| | | a | b | c |
| 80–95 | 0.3 | 11 | 18 | 71 |
| 106 | 0.5 | 26 | 48 | 26 |
| 106–109 | 0.5 | 35 | 59 | 6 |
| 109 | 0.5 | 34 | 64 | 2 |

The fraction boiling between 80° and 95° C. was again subjected to microdistillation to give a fraction consisting of compound (c), boiling point 79° C. at 0.5 mbar.

The NMR spectra of the three compounds showed the following absorptions:

| Compound a | |
| --- | --- |
| $\partial$ = 1.02 ppm (singlet, $H_3C-C-CH_3$) | $\partial$ = 2.24 ppm (singlet, $CH_3-CO$) |
| $\partial$ = 1.13 ppm (singlet, $H_3C-C-CH_3$) | $\partial$ = 3.66 ppm (singlet, $O=C-C(H)-C=O$) |
| $\partial$ = 1.55 ppm (multiplet, $CH-CH_2$) | $\partial$ = 5.62 ppm (doublet, $HC=CCl_2$) |

| Compound b | |
| --- | --- |
| $\partial$ = 0.99 ppm (singlet, $H_3C-C-CH_3$) | $\partial$ = 2.38 ppm (singlet, $CH_3-CO$) |
| $\partial$ = 1.15 ppm (singlet, $H_3C-C-CH_3$) | $\partial$ = 5.58 ppm (doublet, $HC=CCl_2$) |
| $\partial$ = 1.55–2.0 ppm (multiplet, $CH_2-CH$) | |

The infrared spectrum showed an OH-absorption peak at ca 3460 cm$^{-1}$.

| Compound c | |
| --- | --- |
| $\partial$ = 1.02 ppm (singlet, $H_3C-C-CH_3$) | $\partial$ = 2.48 ppm (multplet, $HC-CO$) |
| $\partial$ = 1.15 ppm (singlet, $H_3C-C-CH_3$) | $\partial$ = 3.72 ppm (singlet, $H_3C-O-C=O$) |
| $\partial$ = 1.18 ppm (doublet, $H_3C-CH-CO$); I = 7 Hz | $\partial$ = 5.58 ppm (doublet, $HC=CCl_2$) I = 9 Hz |
| $\partial$ = 1.55 ppm (multiplet, $HC-CH_2-CH$) | |

We claim:

1. A compound of the formula I

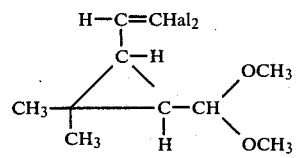

wherein each Hal independently is selected from chlorine, bromine or fluorine.

2. 3-(2,2-Dichlorovinyl)-2,2-dimethylcyclopropanecarbaldehyde dimethyl acetal.

3. A compound according to claims 1 or 2 in the cis isomer form.

* * * * *